United States Patent
Jussel et al.

(10) Patent No.: US 9,518,780 B2
(45) Date of Patent: Dec. 13, 2016

(54) DENTAL FURNACE

(75) Inventors: Rudolf Jussel, Feldkirch-Gisingen (AT); Harald Bürke, Frastanz (AT)

(73) Assignee: Ivoclar Vivadent AG, Schaan (LI)

( * ) Notice: Subject to any disclaimer, the term of this patent is extended or adjusted under 35 U.S.C. 154(b) by 562 days.

(21) Appl. No.: 13/555,333

(22) Filed: Jul. 23, 2012

(65) Prior Publication Data

US 2013/0029280 A1 Jan. 31, 2013

(30) Foreign Application Priority Data

Jul. 25, 2011 (EP) .................................... 11175238

(51) Int. Cl.
| | | |
|---|---|---|
| F27B 11/00 | (2006.01) | |
| F27B 17/02 | (2006.01) | |
| F27B 5/18 | (2006.01) | |
| F27D 19/00 | (2006.01) | |
| F27D 21/00 | (2006.01) | |
| A61C 13/20 | (2006.01) | |

(52) U.S. Cl.
CPC ............ *F27B 17/025* (2013.01); *A61C 13/20* (2013.01); *F27B 5/18* (2013.01); *F27D 19/00* (2013.01); *F27D 21/0014* (2013.01)

(58) Field of Classification Search
CPC .................................................. F27B 17/025
USPC .... 219/390, 405, 406, 407; 432/205, 206, 5, 432/6
See application file for complete search history.

(56) References Cited

U.S. PATENT DOCUMENTS

| | | | |
|---|---|---|---|
| 3,694,122 A * | 9/1972 | MacDonald et al. ......... | 425/171 |
| 4,208,573 A | 6/1980 | Risse | |
| 4,272,670 A * | 6/1981 | Docx ............................ | 219/390 |
| 4,616,123 A | 10/1986 | Zagoroff | |
| 5,498,852 A * | 3/1996 | Cress ............................ | 219/390 |
| 6,157,004 A | 12/2000 | Bizzio | |
| 6,250,367 B1 | 6/2001 | Komuro et al. | |
| 8,109,761 B1 * | 2/2012 | Neal et al. .................... | 432/205 |
| 8,232,506 B2 * | 7/2012 | Jussel .......................... | 219/390 |
| 8,487,220 B2 * | 7/2013 | Serrago et al. ............... | 219/390 |
| 2001/0023056 A1 | 9/2001 | Grunenfelder et al. | |
| 2004/0182438 A1 | 9/2004 | Kobes | |
| 2009/0246739 A1 | 10/2009 | Jussel et al. | |
| 2010/0047731 A1 | 2/2010 | Zubler | |
| 2013/0153561 A1 * | 6/2013 | Jussel .......................... | 219/390 |

FOREIGN PATENT DOCUMENTS

| | | |
|---|---|---|
| DE | 1160777 | 7/1964 |
| DE | 2656316 A1 | 6/1978 |
| DE | 10136584 | 2/2003 |
| DE | 102005015435 | 2/2007 |
| EP | 1457167 A1 | 9/2004 |
| JP | 2004057922 A | 2/2004 |

(Continued)

*Primary Examiner* — Gregory A Wilson
(74) *Attorney, Agent, or Firm* — Ann M. Knab; Thad McMurray

(57) ABSTRACT

A dental furnace (10) for dental restorations comprising a firing chamber into which, in particular between a furnace bottom part (14) and a furnace upper part (12), the dental restoration, in particular within a muffle, can be introduced, and a sensor that is connected with a control device (52) for the dental furnace (10), wherein the sensor, in particular the temperature sensor (22), is arranged outside the firing chamber and comprises a detection range (40) that also extends outside the firing chamber.

22 Claims, 1 Drawing Sheet

(56) References Cited

FOREIGN PATENT DOCUMENTS

| RU | 2063727 | C1 | 7/1996 |
| RU | 2088898 | C1 | 8/1997 |
| RU | 2374692 | C2 | 11/2009 |

* cited by examiner

DENTAL FURNACE

CROSS-REFERENCE TO RELATED APPLICATIONS

This application claims the benefit of European Patent Application No. 11175238.2 filed on Jul. 25, 2011, which is hereby incorporated by reference in its entirety.

TECHNICAL FIELD

The present invention relates to a dental furnace for dental restorations.

BACKGROUND

Dental furnaces with temperature control devices have been used in the industry for a long time. Thus, it is for example already provided in DE 1 160 777 to keep the temperature in the muffle furnace constant. A muffle furnace of this kind serves to fire a dental restoration part in a muffle that comprises a negative mold of the dental restoration part that is to be achieved. In the illustrated solution, a pre-heating chamber is provided below the actual firing chamber, and the heating power of the local firing chamber heating is controlled or driven via a continuous transformer. A "chopper bar" controller that may be regarded as a precursor of a PID controller, controls the heating power.

The solution described in the aforementioned patent specification is rather complicated or cumbersome if it is necessary to provide a quick cycle time for dental restoration parts and an ergonomically favorable workflow. This is due to the fact that a pre-heating zone is integrated there so that a cold muffle must typically be only heated there before it can be subjected to the firing cycle by insertion thereof into the press chamber.

However, it is particularly disadvantageous that in this solution the furnace head rests on fixed columns and remains stationary whereas the sensitive dental restoration part must be moved. This solution is indeed quite low-priced but it does not meet higher quality standards unless an extremely long cycle time is aimed for, during which the dental furnace completely cools down until the firing cycle is completed.

In case of modern dental furnaces, however, it is important to realize a shorter cycle time also when casting or pressing multi-unit bridges. Press furnaces in which a press stamp or plunger presses a green body into a channel in the muffle and the dental restoration part is produced in the negative mold as soon as the pressed article or blank that is also referred to as green body, liquefies, enable a high-quality production of a dental restoration part in a short cycle time.

The temperature control of firing furnaces and press furnaces for the dental technology has basically been employed unchanged for several decades. As a further example for the use of a thermocouple element in combination with a temperature controller DE 26 56 316 is to be mentioned.

Also DE 101 36 584 A1 illustrates a dental furnace comprising a muffle, the special feature in this case being the fact that the temperature sensor quasi penetrates into the muffle and is to detect the temperature thereof. For this purpose, however, a specific muffle form is necessary which is not compatible with commercially available muffles. Moreover, when realizing the particular recesses in the muffle, it has to be paid attention to the fact that the cavities for the dental restoration parts do not get too close to said recesses since at a corresponding high press power of the press stamp or plunger the muffle can form a crack at this location due to the weakening there.

A precise temperature control can thus be better achieved with the solution according to DE 10 2005 015 435 A1 in which a temperature sensor that is basically spaced apart from the muffle, measures the temperature thereof according to the type of a pyrometer for example. The temperature measurement is carried out at a position which is clearly spaced apart from the surface facing the heating elements so that the true muffle temperature is detected.

SUMMARY

The present invention is based upon the object of producing a dental furnace for dental restorations with regard to the handling and the cycle time thereof. The attached claims are incorporated by reference herein.

According to an embodiment of the invention it is particularly favorable if in addition to the temperature sensor that is directed towards the dental restoration part, or instead thereof, a temperature sensor is provided that is arranged outside the firing chamber and that detects the temperature of objects approaching the dental furnace. For this purpose, the temperature sensor comprises a given detection range, that is to say a range in which it responds to an elevated temperature compared to room temperature and signalizes that an object having an elevated temperature is located there.

This surprisingly simple measure may inventively be used for the opening of the dental furnace upon the approach of a hot object such as a hot dental restoration part or a muffle that has already been pre-heated in a pre-heating furnace, which opening permits the insertion of the dental restoration part or the muffle.

The dental furnace preferably comprises a furnace hood that accommodates the heating of the dental furnace, as well as a furnace bottom part that is arranged stationary. The furnace hood is connected via a furnace pivoting arrangement with the furnace bottom part.

Upon the approach of a hot object, the furnace hood is quickly lifted via a motor so that the dental technician or the dentist immediately can place or put down the object such as for example the pre-heated muffle, on the firing chamber floor.

Even if this arrangement having the movable furnace hood is preferred, it is to be understood that instead also an arrangement is possible without further delay or complications in which the furnace hood remains stationary and the firing chamber floor is lowered. It is also conceivable to provide an automatic opening of a door for the firing chamber via which the muffle may then be inserted.

According to an embodiment of the invention it is particularly favorable if the detection range of the temperature sensor or probe already starts at a clear distance from the dental furnace. Preferably the detection range is oriented so that it extends laterally at an inclination in front of the furnace hood. In case of a fluent or smooth movement with an approach of the hot muffle, there then remains enough time until the furnace hood is opened by motor actuation. The opening can take place within one second for example, and the dental technician requires little more than one second in order to move the hot muffle for example 80 cm at an inclination towards the furnace hood.

The detection range can easily be quite narrow when regarded both in the vertical and also horizontal direction as the dental technician can then move the hot muffle into said detection range in a targeted manner in order to open the dental furnace.

It is to be understood that a detection range over a dihedral angle of 90° or more may be realized instead; in case of adjacently arranged dental furnaces it is to be understood that it is advantageous to reduce the extension of the detection range to clearly less, for example to 50°, in order not to inadvertently produce a simultaneous triggering of several dental furnaces with the hot muffle.

In an inventively particularly preferred arrangement, a reflector for temperature radiations is arranged at the furnace hood which reflector extends at an oblique angle relative to the optical axis of the temperature sensor.

The reflector can readily be formed by some kind of sheet metal strip that can be somewhat bent into shape as desired by the dental technician in order to adapt the detection range to meet his personal needs. It is to be understood that the reflector is selected so that it particularly well reflects infrared radiation, i.e., radiation within the wavelength area about 800 nm.

It is also readily possible to attach the temperature sensor at a different position to the dental firing furnace. For example it can be attached outside of the furnace hood and can comprise a detection range laterally extending away from it. Alternatively, the temperature sensor can be attached to the furnace bottom part, and the detection range then substantially extends vertically upwards or obliquely outwards/upwards relative to the vertical axis of the dental furnace, respectively.

The arrangement of the reflector basically has the advantage that the temperature sensor is essentially better protected, especially, if hot parts spatter away for example, as they then only hit the reflector which is formed by a sheet metal strip or a metal plate.

Moreover, this solution also enables the multifunctional use of the temperature sensor. If the temperature sensor is supported in a fixed manner, i.e. it is fixedly connected with the furnace bottom part, and is directed furnace-inward, it can serve as a proximity sensor if the furnace hood is closed as the heat radiation reflected by the reflector then impinges on the temperature sensor.

However, if the furnace hood is opened, the detection range of the temperature sensor is directed furnace-inward, for example towards the muffle located there or a dental restoration part, so that its temperature can then easily be detected.

A commercially available infrared sensor can be used as a temperature sensor that detects the approach of a hot muffle, i.e., a muffle with a temperature of for example more than 500° C. Alternatively, it is also possible to employ a thermal imaging camera or any other camera which is sensitive in the infrared range. It is also possible to use an array of infrared-sensitive diodes which responds to temperatures of the muffle between approximately 300° C. and approximately 850° C.

If a configuration is selected in which the temperature detection element detects the temperature in the detection range via a reflector that is fixed to the furnace hood, it is important that the temperature detection element is protected against the waste heat of the firing chamber in case of an open furnace hood. This can be realized by either selecting a respective suitable distance of the temperature detection element from the furnace hood, or by a blind that acts in a heat-insulating manner and merely comprises a quite small opening that extends somewhat spaced apart from the infrared sensor at the angle of the detection range in front thereof and that blocks the furnace radiation emitted by the open furnace hood in the direction towards the temperature sensor.

According to an embodiment of the invention it is particularly favorable that with the aid of the invention a contact-free operation can be realized for the first time, and in fact in a targeted manner exactly then, when the dental furnace is to be opened.

In a modified embodiment, the sensor is formed as a proximity sensor that permits the opening of the furnace upon approach of the muffle. In case of this configuration it is particularly preferred if at least one further distinctive feature such as a bar code, the iris of the user or anything like that, enables a further identification and differentiation from an inadvertent approach.

In an advantageous arrangement it is provided that the control device prior to the opening of the dental furnace based on the output signal of the temperature sensor verifies if the firing chamber comprises a sufficient temperature for the accommodation of the object of the muffle.

In a further advantageous embodiment it is provided that the dental furnace is formed as a muffle press furnace for dental restoration parts, and that the firing chamber is adapted to accommodate a muffle, and that an object that is to be detected in the detection range is a muffle of the muffle press furnace.

In a further advantageous embodiment it is provided that the control device carries out a specific control function if a muffle or a dental restoration part, in particular, on a carrier, reaches the detection range of the temperature sensor.

In a further advantageous embodiment it is provided that the control function comprises a function that is associated with the start of a firing operation of the dental furnace, for example the switching on of the dental furnace, but in particular, the opening of the dental furnace.

In a further advantageous embodiment it is provided that the detection range of the temperature sensor enlarges in a direction transverse to the temperature sensor if starting from the temperature sensor, and that the detection range extends obliquely to a lateral surface of the dental furnace.

In a further advantageous embodiment it is provided that the detection range of the temperature sensor extends along the furnace upper part, that in particular, the detection range of the temperature sensor substantially extends horizontally or obliquely upwards or obliquely downwards and covers a range to the side of the furnace upper part.

In a further advantageous embodiment it is provided that the temperature sensor is attached to the furnace bottom part and that the detection range of the sensor extends about the optical axis of the sensor, in particular upwards.

In a further advantageous embodiment it is provided that the detection range of the temperature sensor, starting from the furnace bottom part, extends upwards or obliquely upwards along the furnace upper part.

In a further advantageous embodiment it is provided that the temperature sensor with its optical axis faces towards the furnace and that the optical axis of the temperature sensor hits a reflector that is formed in a suitable manner for reflecting the heat radiation that impinges on the temperature sensor.

In a further advantageous embodiment it is provided that the optical axis of the temperature sensor intersects the vertical axis of the firing chamber in the furnace upper part or extends at an angle that deviates at most 15° C. from a straight line that connects the vertical axis with the temperature sensor.

In a further advantageous embodiment it is provided that the temperature sensor comprises a spectral sensitivity whose focus lies in the infrared wavelength range, and responds to objects that are located within the detection range and have an elevated temperature, i.e., a notably higher temperature than room temperature, in particular, more than 100° C. and in particular preferably more than 300° C.

In a further advantageous embodiment it is provided that the temperature sensor is formed according to the type of a thermal imaging camera that detects image information of the objects located within the detection range as far as they exhibit an elevated temperature.

In a further advantageous embodiment it is provided that the control device opens the dental furnace when the temperature sensor detects the presence of an object having an elevated temperature in the detection range.

In a further advantageous embodiment it is provided that the temperature sensor comprises a detection range which is subdivided into two subdetection ranges, and that the control device opens the dental furnace when the temperature sensor first detects an object in the first subdetection range that is more distant from the furnace, and subsequently detects the object in a detection range that is closer to the furnace, i.e., the temperature sensor detects a certain approach of the object to the furnace.

In a further advantageous embodiment it is provided that the temperature sensor is embodied as a one- or two-dimensional field of infrared-sensitive diodes and that the temperature sensor is arranged at least ten centimeters away from the firing chamber.

In a further advantageous embodiment the sensor is arranged outside the firing chamber and comprises a detection range that also extends outside the firing chamber, and the sensor is further formed as a proximity sensor and in particular at least one further sensor detects and recognizes the approaching object and/or the user of the dental furnace.

BRIEF DESCRIPTION OF THE DRAWINGS

Embodiments of the present invention will be more fully understood and appreciated by the following Detailed Description in conjunction with the accompanying drawings, in which.

DETAILED DESCRIPTION

Figure 1:
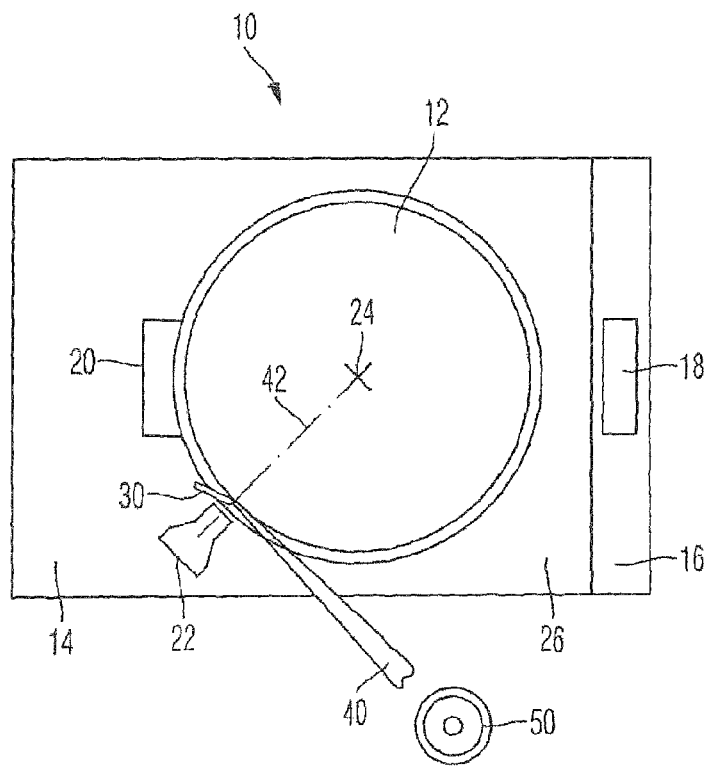
FIG. 1 illustrates a schematic view of an inventive dental furnace in one exemplary embodiment of the invention.

The dental furnace 10 illustrated in FIG. 1 comprises a furnace hood 12 as a furnace upper part, as well as a furnace bottom part 14. It is configured as a muffle press furnace, and the circular furnace hood 12 forms inside in a firing chamber, whose diameter is also sufficient for accommodating the likewise circular and substantially cylindrical muffle.

The furnace bottom part comprises an inclined plane 16 which supports a touch-sensitive display 18 via which the inventive dental furnace 10 can be actuated.

The furnace hood 12 is supported in a manner known per se on the furnace lower part 14 via a lifting/pivoting device so that it may be lifted off the furnace lower part and swung open by leaving a gap. In also a manner known per se, the furnace can perform a firing operation by switching on the heating in the furnace hood with the furnace hood being closed and by inserting a press stamp or plunger into the muffle with the muffle being heated, said press stamp or plunger pressing the dental restoration material in the muffle into prepared mold cavities.

According to an embodiment of the invention it is provided that a temperature sensor 22 is supportedly attached to the furnace bottom part which sensor is directed towards the vertical axis 24 of the dental furnace. The support of the temperature sensor 22 is immediately effected on the upper side 26 of the furnace bottom part 14, i.e., at the lower end of the furnace hood 12.

Further, a reflector 30 is attached to the outer periphery of the furnace hood 14 next to the temperature sensor 22.

The reflector 30 is formed as a sheet metal strip, for example from aluminum foil, or as some other metal plate and is suitable for reflecting the heat radiation. It extends away from the furnace hood at a slight angle, for example at an angle of 45°. It is to be understood that the exact orientation can be adapted to the requirements within wide ranges.

In case of a tilt angle of 45° of the reflector, a detection range 40 extends at an angle of 90° relative to the optical axis 42 of the temperature sensor 22. It is to be understood that the detection range 40 conically widens or expands in a manner known per se. Preferably a quite strong bunching is provided that enables a particularly sensitive detection of the temperature also in case of a larger distance. The bunching can also be improved by forming the reflector 30 according to the type of a concave mirror.

In the illustrated exemplary embodiment a muffle 50 is schematically illustrated at a position in which the heat radiation emitted by it lies within the detection range 40 of the temperature sensor 22.

The muffle has previously been heated in a pre-heating furnace to a temperature of 700° C. and still has a temperature of approximately 500° C. at its outside. The heat radiation emitted by the muffle now impinges on the temperature sensor 22 in the detection range 40 via the reflector 30. The temperature sensor 22 is electrically connected to a control device 52 that is preferably received within the furnace bottom part 14. In case of the approach of the hot muffle 50, the control device triggers an opening signal for the lifting/pivoting device 20 which, activated by the signal, lifts the furnace hood 12 and enables the muffle 50 to be placed on the furnace bottom part below the optical axis 42, and the movement of the muffle 50 towards the dental furnace does not have to be decelerated.

It is to be understood that the connection between the temperature sensor 22 and the control device 52 can be formed in any suitable manner. The temperature sensor 22 is in fact fixedly installed on a base, preferably is attached to the dental furnace, but is electrically connected to the control device in any suitable manner, such as for example by radio, by Bluetooth or via an infrared connection, or via an electric line in a manner known per se.

It is to be understood that the orientation of the detection range can be effected in any suitable manner. If necessary, also several reflectors 30 can for example be attached to the furnace hood 12 as a standard. Moreover, the temperature sensor 22 may be positioned at several possible attachment positions. The dental technician, even also as a left-hander for example, can then install the temperature sensor 22 in any suitable manner and can automatically start the opening upon an approach of the muffle 50 to the dental furnace 10.

Figure 2:
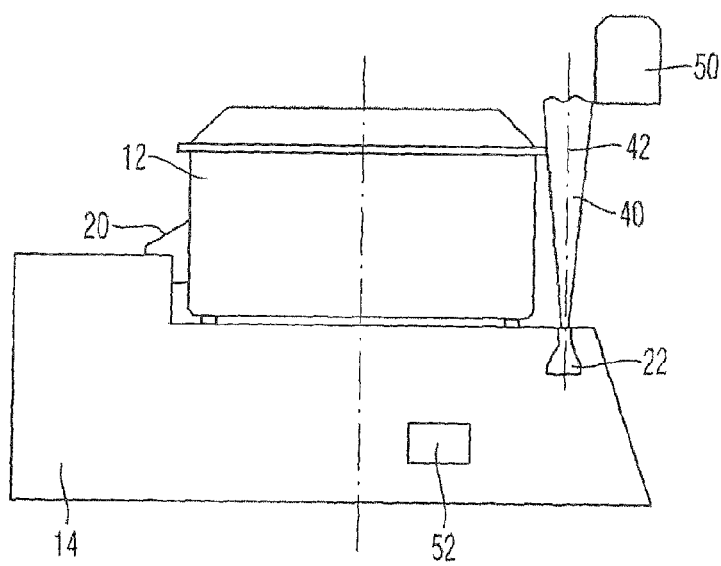
FIG. 2 illustrates a side view of a further embodiment of a dental furnace according to the invention.

FIG. 2 shows a modified embodiment of a dental furnace. The same reference numerals indicate the same or corresponding components.

In contrast to the embodiment according to FIG. 1, the detection range 40 of the temperature sensor 22 is substantially aligned vertically. The optical axis 42 of the temperature sensor 22 extends, starting from the furnace lower part 14, vertically upwards, for example at an oblique angle laterally in front of the furnace hood 12.

It is to be understood that also in this case several attachment possibilities for the temperature sensor 22 can be provided if necessary that enable the modification of the detection range at the option of the dental technician. In this case, too, the triggering of the temperature sensor 22 is effected by the fact that the muffle 50 at least partially enters the detection range 40 and that the heat radiation emitted by the muffle 50 lifts the furnace hood 12 via the control device 52 in the furnace bottom part.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A dental furnace for dental restorations comprising
a furnace bottom part,
a furnace upper part,
a firing chamber having a muffle into which the dental restoration can be introduced, and
a temperature sensor that is connected with a control device for the dental furnace,
wherein the temperature sensor is arranged outside the firing chamber and comprises a detection range that also extends outside the firing chamber,
wherein the temperature sensor responds to objects that are located within the detection range and which have an elevated temperature, and
wherein the detection range of the temperature sensor enlarges in a direction transverse to the temperature sensor if starting from the temperature sensor, and that the detection range extends obliquely to a lateral surface of the dental furnace.

2. The dental furnace according to claim 1,
wherein the dental furnace is formed as a muffle press furnace for dental restoration parts,
wherein the firing chamber is adapted for the accommodation of a muffle and
wherein an object that is to be detected in the detection range comprises the muffle of the muffle press furnace.

3. The dental furnace according to claim 1,
wherein the control device performs a special control function if the muffle or the dental restoration reaches the detection range of the sensor.

4. The dental furnace according to claim 3,
wherein the control function includes a function that is associated with a start of a firing process of the dental furnace.

5. The dental furnace according to claim 4,
wherein the start of the firing process comprises switching on of the dental furnace.

6. The dental furnace according to claim 5,
wherein the switching on of the dental furnace comprises opening of the dental furnace.

7. The dental furnace according to claim 1,
wherein the detection range of the temperature sensor extends along the furnace upper part.

8. The dental furnace according to claim 1,
wherein the detection range of the temperature sensor substantially extends horizontally or obliquely upwards or obliquely downwards and covers an area to the side of the furnace upper part.

9. The dental furnace according to claim 1,
wherein the temperature sensor is attached to the furnace bottom part and
wherein the detection range of the sensor extends upwards about the optical axis of the sensor.

10. The dental furnace according claim 1,
wherein the detection range of the temperature sensor, starting from the furnace bottom part, extends upwards or obliquely upwards along the furnace upper part.

11. The dental furnace according to claim 1,
wherein the temperature sensor has an optical axis facing towards the furnace and
wherein the optical axis of the temperature sensor hits a reflector that is formed in a manner for reflecting the heat radiation that impinges on the temperature sensor.

12. The dental furnace according to claim 1,
wherein the optical axis of the temperature sensor intersects the vertical axis of the firing chamber in the furnace upper part or extends at an angle that deviates at most 15° C. from a straight line that connects the vertical axis with the temperature sensor.

13. The dental furnace according to claim 1,
wherein the temperature sensor comprises a spectral sensitivity with a focus in the infrared wavelength range.

14. The dental furnace according to claim 1,
wherein the elevated temperature is a higher temperature than room temperature.

15. The dental furnace according to claim 14,
wherein the elevated temperature is more than 100° C.

16. The dental furnace according to claim 14,
wherein the elevated temperature is more than 300° C.

17. The dental furnace according to claim 1,
wherein the temperature sensor is a thermal imaging camera that detects image information of objects located within the detection range as far as they exhibit an elevated temperature.

18. The dental furnace according to claim 1,
wherein the control device opens the dental furnace when the temperature sensor detects the presence of an object having an elevated temperature in the detection range.

19. The dental furnace according to claim 1,
wherein the temperature sensor comprises a detection range which is subdivided into two subdetection ranges, and
wherein the control device opens the dental furnace when the temperature sensor first detects an object in the first subdetection range that is more distant from the furnace, and subsequently detects the object in a detection range that is closer to the furnace.

20. The dental furnace according to claim 1,
wherein the temperature sensor detects a certain approach of an object to the furnace.

21. The dental furnace according claim 1,
wherein the temperature sensor is embodied as a one- or two-dimensional field of infrared-sensitive diodes and
wherein the temperature sensor is arranged at least ten centimeters away from the firing chamber.

22. A dental furnace for dental restorations comprising
a furnace bottom part,
a furnace upper part,
a firing chamber into which the dental restorations can be introduced, a first sensor that is connected to a control device for the dental furnace,
a second sensor for detecting and recognizing at least one of an approaching object and the user of the dental furnace,
wherein the first sensor is arranged outside the firing chamber and comprises a detection range that also extends outside the firing chamber,
wherein the first sensor is formed as a proximity sensor, and
wherein the detection range of the first sensor enlarges in a direction transverse to the first sensor if starting from the first sensor, and that the detection range extends obliquely to a lateral surface of the dental furnace.

* * * * *